United States Patent
Alameh et al.

(10) Patent No.: US 11,761,886 B2
(45) Date of Patent: *Sep. 19, 2023

(54) DETECTION SYSTEM FOR DETECTING MATTER AND DISTINGUISHING SPECIFIC MATTER FROM OTHER MATTER

(71) Applicant: Photonic Detection Systems Pty Ltd, Kingsley (AU)

(72) Inventors: Kamal Alameh, Joondalup (AU); Selam Ahderom, Joondalup (AU)

(73) Assignee: Photonic Detection Systems Pty Ltd, Kingsley (AU)

( * ) Notice: Subject to any disclaimer, the term of this patent is extended or adjusted under 35 U.S.C. 154(b) by 289 days.

This patent is subject to a terminal disclaimer.

(21) Appl. No.: 17/260,531

(22) PCT Filed: Nov. 23, 2018

(86) PCT No.: PCT/AU2018/051252
§ 371 (c)(1),
(2) Date: Jan. 14, 2021

(87) PCT Pub. No.: WO2020/014728
PCT Pub. Date: Jan. 23, 2020

(65) Prior Publication Data
US 2021/0381959 A1 Dec. 9, 2021

(30) Foreign Application Priority Data
Jul. 17, 2018 (AU) .................. 2018902590

(51) Int. Cl.
*G01N 21/31* (2006.01)
*G01B 11/24* (2006.01)
(Continued)

(52) U.S. Cl.
CPC ............ *G01N 21/31* (2013.01); *G01B 11/24* (2013.01); *G01N 21/84* (2013.01); (Continued)

(58) Field of Classification Search
CPC ............... A01M 7/0089; G01B 11/24; G01N 2021/3148; G01N 2021/8466; (Continued)

(56) References Cited

U.S. PATENT DOCUMENTS

| 5,296,702 A | 3/1994 | Beck et al. |
| 5,900,634 A | 5/1999 | Soloman |

(Continued)

FOREIGN PATENT DOCUMENTS

| WO | 1999/030133 A1 | 6/1999 |
| WO | 2008/014553 A1 | 2/2008 |

(Continued)

OTHER PUBLICATIONS

The Extended European Search Report issued for European Patent Application No. 18926635.6, dated Feb. 23, 2022 in 8 pages.

(Continued)

*Primary Examiner* — Tri T Ton
(74) *Attorney, Agent, or Firm* — Knobbe, Martens, Olson & Bear, LLP

(57) ABSTRACT

The present disclosure provides a detection system for detecting matter and distinguishing specific matter from other matter. The detection system comprises at least one light source arranged to emit one or more light beams having a known wavelength or wavelength range. Further, the detection system comprises at least one optical element configured to direct the one or more light beams onto a plurality of locations within an area of interest including the matter. The detection system also comprises a detector for detecting intensities of the one or more light beams reflected (Continued)

at the plurality of locations within the area of interest including the matter. In addition, the detection system comprises an outcome determination system. The system is arranged to obtain information indicative of at least a portion of a shape of at least some of the matter based on detected light intensities of the one or more light beams reflected at the plurality of locations. The system is also arranged to obtain information indicative of a spectral intensity distribution based on detected light intensities of the one or more light beams reflected at the plurality of locations. The outcome determination system is arranged determine whether the matter is specific matter based on the information indicative of at least a portion of a shape of at least some of the matter and based on the information indicative of a spectral intensity distribution.

8 Claims, 5 Drawing Sheets

(51) Int. Cl.
| | | |
|---|---|---|
| *G01N 21/84* | (2006.01) | |
| *G01N 33/00* | (2006.01) | |
| *G06N 3/02* | (2006.01) | |
| *G06V 10/145* | (2022.01) | |
| *A01M 7/00* | (2006.01) | |
| *G06V 20/68* | (2022.01) | |

(52) U.S. Cl.
CPC ........... *G01N 33/0098* (2013.01); *G06N 3/02* (2013.01); *G06V 10/145* (2022.01); *A01M 7/0089* (2013.01); *G01N 2021/8466* (2013.01); *G01N 2201/0612* (2013.01); *G06V 20/68* (2022.01)

(58) Field of Classification Search
CPC ...... G01N 21/255; G01N 21/31; G01N 21/84; G01N 2201/0612; G01N 33/0098; G01N 2201/1296; G06N 3/02; G06N 3/08; G06V 10/145; G06V 20/68
USPC .................................................. 356/244, 256
See application file for complete search history.

(56) References Cited

U.S. PATENT DOCUMENTS

| | | | |
|---|---|---|---|
| 6,443,365 B1 * | 9/2002 | Tucker | ................. B05B 12/122 239/69 |
| 2004/0014989 A1 | 8/2004 | Scott | |
| 2010/0014096 A1 | 1/2010 | Alameh | |
| 2021/0124960 A1 * | 4/2021 | Lee | ..................... G06V 10/145 |
| 2021/0270792 A1 * | 9/2021 | Alameh | ................ G01J 3/0205 |

FOREIGN PATENT DOCUMENTS

| | | |
|---|---|---|
| WO | 2011/143686 A1 | 11/2011 |
| WO | 2017/194399 A1 | 11/2017 |

OTHER PUBLICATIONS

International Preliminary Report on Patentability for International Patent Application No. PCT/AU2018/051252, dated Jul. 1, 2019 in 14 pages.

* cited by examiner

DETECTION SYSTEM FOR DETECTING MATTER AND DISTINGUISHING SPECIFIC MATTER FROM OTHER MATTER

CROSS-REFERENCE TO RELATED APPLICATIONS

This application is the U.S. National Phase under 35. U.S.C. § 371 of International Application PCT/AU2018/051252, filed Nov. 23, 2018, which claims priority to Australian Patent Application No. 2018902590, filed Jul. 17, 2018. The disclosures of the above-described applications are hereby incorporated by reference in their entirety.

TECHNICAL FIELD

The present disclosure relates to a detection system for detecting matter and distinguishing specific matter from other matter. The matter may be, but is not limited to, plant matter and the specific plant matter may include weeds.

BACKGROUND

The control of weed growth is an important factor in agriculture. Large areas of plant matter including valuable plants, such as crops, and weeds are usually sprayed with expensive and toxic chemicals in order to control (restrain) the weed growth. Ideally only the weeds should be sprayed, but this is difficult if the weeds grow amongst the valuable plant matter. It may also be useful to be able to distinguish in an automated manner particular plant matter from other matter so that the particular plant matter can be treated differently to the other matter.

PCT International Application Number PCT/AU2007/001075, owned by the present applicant, discloses an optical device for discriminating specific plant matter from other matter. The optical device comprises laser diodes that emit light having three wavelengths and a plurality of light beams. Each light beam has the three wavelengths sequentially directed to the plant matter. A detector detects light beams that are reflected back from the plant matter. A processor then processes the reflected intensities and compares the detected intensity ratios at the three wavelengths with a library of such intensity ratios of known plant matter whereby the device is enabled to discriminate a particular type of plant matter from other matter.

WO 2011/143686 A1, also owned by the present applicant, discloses an automated device that is able to distinguish weeds from the valuable plant matter in a quick manner to restrict the spraying of the chemicals to the weeds only.

The present disclosure provides a further technological improvement.

SUMMARY OF INVENTION

According to a first aspect of the invention, there is provided a detection system for detecting matter and distinguishing specific matter from other matter, the detection system comprising:

at least one light source arranged to emit one or more light beams having a known wavelength or wavelength range;

at least one optical element configured to direct the one or more light beams onto a plurality of locations within an area of interest including the matter;

a detector for detecting intensities of the one or more light beams reflected at the plurality of locations within the area of interest including the matter;

an outcome determination system;

wherein the system is arranged to obtain information indicative of at least a portion of a shape of at least some of the matter based on detected light intensities of the one or more light beams reflected at the plurality of locations;

wherein the system is arranged to obtain information indicative of a spectral intensity distribution based on detected light intensities of the one or more light beams reflected at the plurality of locations; and wherein the outcome determination system is arranged determine whether the matter is specific matter based on the information indicative of at least a portion of a shape of at least some of the matter and based on the information indicative of a spectral intensity distribution.

The matter may be plant matter.

The specific matter may be or may include a weed.

The at least one optical element may be configured to direct a plurality of light beams onto the plurality of locations.

The at least one optical element may be configured to arrange the plurality of light beams in a row.

The system may be configured to scan the area of interest with the row of light beams in a direction substantially perpendicular to the row, such that each light beam is directed to two or more of the plurality of locations.

The light beams of the plurality of light beams may be distributed in a 2-dimensional manner.

The 2-dimensional manner may be an array.

The array may be an array of N×M light beams, where A is an integer between 1 and 50, and B is an integer between 1 and 50.

The outcome determination system may be configured to receive a plurality of inputs, wherein each input comprises information indicative of an intensity of light detected at one of the plurality of locations.

The light source may be capable of emitting light having at least 3 wavelengths, and wherein the outcome determination system is arranged to determine ratios of detected intensities at the three wavelengths.

The outcome determination system may be arranged to determine whether the matter is specific matter by receiving a plurality of inputs, each input corresponding to one of the one or more light beams reflected at the plurality of locations, wherein each input comprises:

information indicative of an intensity, or a ratio of intensities, of the respective light beam; and information indicative of a location at which the one light beam is reflected.

It is believed that by combining two types of information, namely laser intensity information and information concerning a shape of the matter, rather than relying on only one type of information, specific matter can be more accurately identified. Advantageously, if one type of information does not adequately distinguish between the specific matter and other matter, the other type of information may still make the distinction. For example, if a particular type of weed and crop have similar shapes, the system may still distinguish between the weed and crop on the basis of intensities.

The outcome determination system may be configured to determine whether the matter is specific matter using an artificial neural network.

DETAILED DESCRIPTION

Figure 1:
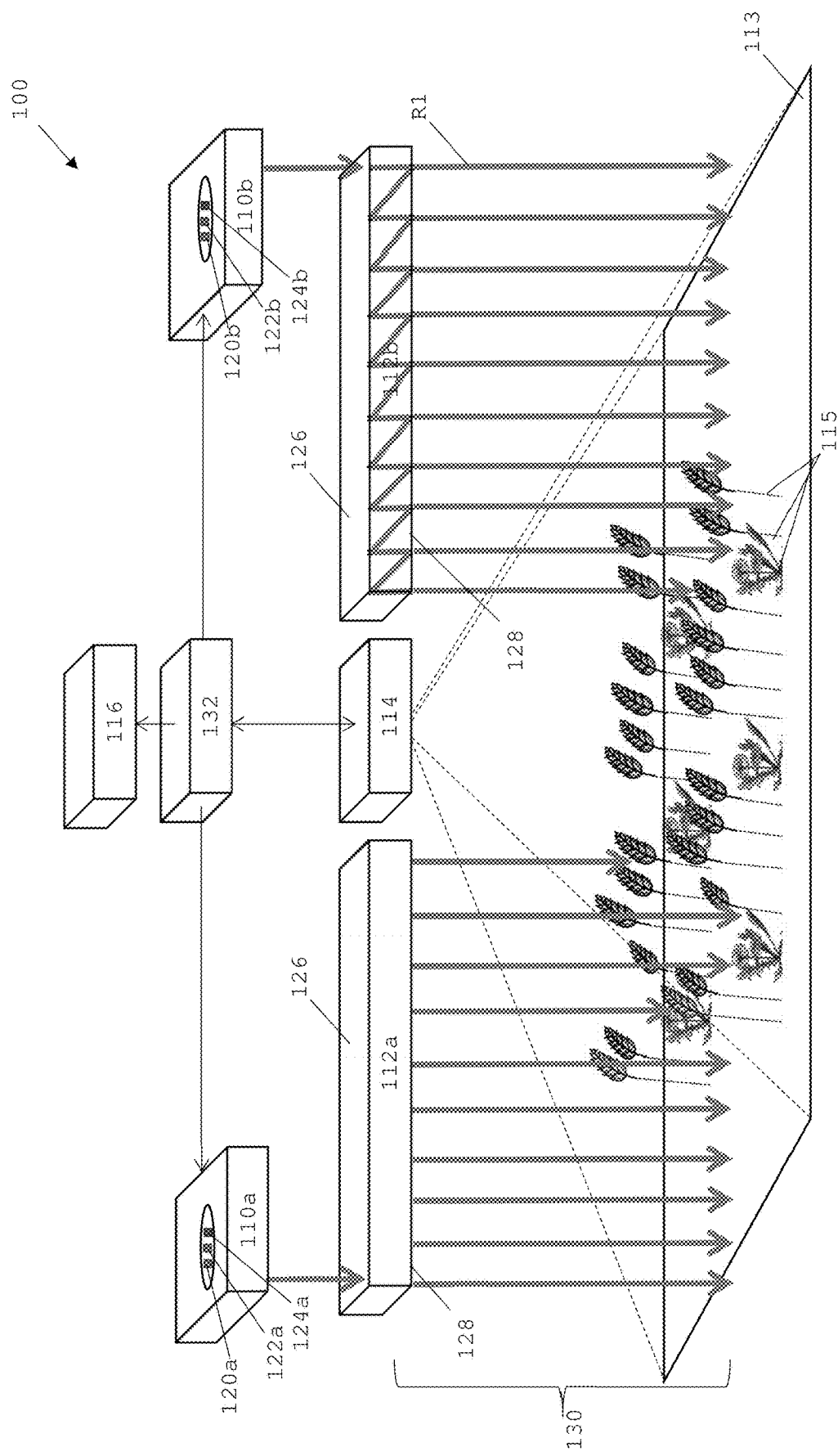
FIG. 1 is a schematic diagram of a detection system in accordance with an embodiment of the present invention.

FIG. 1 shows an embodiment of a detection system 100 for detecting matter and distinguishing specific matter from other matter. In this example, the matter is plant matter, and the specific matter is weed. However, it will be appreciated that the matter and specific matter can be other types of matter.

The system 100 includes components that are related to a device disclosed in WO 2011/143686 A1, which is incorporated herein by reference.

The system 100 comprises light sources 110a, 110b arranged to emit one or more light beams having a known wavelength or wavelength range. The system 100 also comprises optical elements 112a, 112b configured to direct the light beams onto a plurality of locations within an area of interest 113 including the plant matter.

The system 100 further comprises a detector 114 for detecting an intensity of the one or more light beams reflected at the plurality of locations within the area of interest. In this regard, it is known that different types of plant matter, such as crops and weeds, can be distinguished on the basis of intensities of light reflected from them.

In addition, the system 100 is arranged to obtain information indicative of at least a portion of a shape of at least some of the matter based on the light beams reflected at the plurality of locations. In this example, the information is also based on the intensity of the light reflected at the plurality of locations.

The system 100 further comprises an outcome determination system 116. As will also be described in more detail below, the outcome determination system 116 is arranged to determine whether the plant matter is specific matter based on: (a) the detected intensities, and (b) the information indicative of the shape of the specific plant matter of the matter.

Specific components of the system 100 will now be described.

In this example, the system 100 is arranged to emit a plurality of light beams distributed in a row 'R1'. In particular, the system 100 comprises a first light source 110a and a second light source 112b. The system 100 further comprises two optical elements: a first optical element 112a and a second optical element 112b. In this example, each optical element 112a, 112b is implemented as an optical cavity. The first optical element 112a is arranged to receive a light beam from the first light source $110a_N$. The second optical element 112b is arranged to receive a light beam from the second light sources 110b.

In this example, the first and second light sources 110a and 110b are considered as a pair of light sources. Each light source 110a, 110b in the pair comprises three laser diodes each capable of generating light at different wavelengths. In particular, the first light source 110a includes a first laser diode 120a generating light having a first wavelength of 635 nm, a second laser diode 122a, generating light having a second wavelength of 670 nm or 685 nm and a third laser diode 124a generating light having a third wavelength of 785 nm. Similarly, the second light source 110b includes a first laser diode 120b generating light having a first wavelength of 635 nm, a second laser diode 122b, generating light having a second wavelength of 670 nm or 785 nm and a third laser diode 124b generating light having a third wavelength of 785 nm.

The laser diodes 120a, 122a, 124a from the first light source 110a emit pulses of laser light in sequence. The pulses may be for any suitable length of time, such as but not limited to 200 microseconds. The laser pulses from each diode 120a, 122a, 124a are directed by a beam combiner (not shown) in the same direction towards the optical element 112a, such that the sequence of laser pulses form a single stream or light beam. The laser diodes 120b, 122b, 124b from the second light source 110b are arranged in the same manner. Furthermore, pairs of corresponding lasers 120a/b, 122a/b, 124a/b, one from each light source 110a, 110b which emit light having the same wavelength, are operated together and in sequence with other pairs of corresponding lasers.

Each optical cavity of the optical elements 112a, 112b has opposite reflective coatings 126 and 128. The reflective coatings 126, 128 have a relatively high reflectivity, such as 99% or higher. Light from respective light sources 110a, 110b is transmitted toward the optical elements 120a, 120b and reflected between the reflective coatings 126, 128 in a zigzag manner (illustrated particularly in the optical element 112b, but not shown for the element 112a, in FIG. 1). However, the reflective coatings 128 on a lower surface of the optical elements 112a, 112b have lower reflectivities than the reflective coatings 126 on an upper surface of the optical elements 112a, 112b. Thus, a portion of light is transmitted through the reflective coatings 128 and a series of component light beams 130 is formed in the row R1, and directed in a substantially parallel manner towards plant matter 115.

Figure 2:
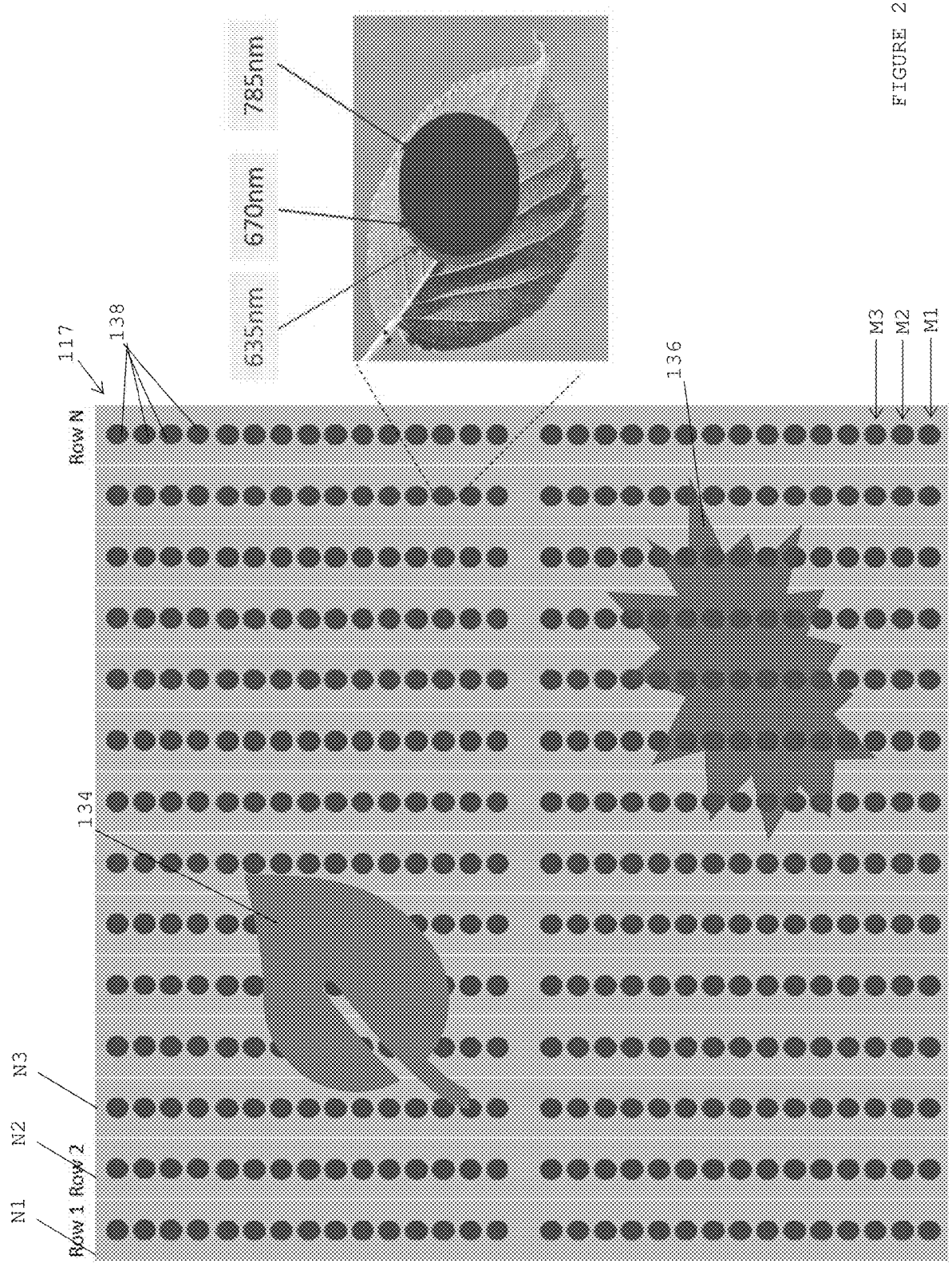
FIG. 2 is a schematic illustration of light beam spots produced by using an embodiment of the detection system.

In this example, the light sources 110a, 110b and respective optical elements 112a, 112b of the system 100 are movable so that the component light beams 130 traverse across the area of interest 113. In particular, the light sources 110a, 110b and respective optical elements 112a, 112b move in a direction substantially perpendicular to the row R1 of component light beams 130. Each component light beam 130 thus traverses across a plurality of locations along a respective line (or column). With reference to FIG. 2, the detector 114 can thus detect intensities of component light beams 130 reflected from a 2-dimensional array of locations 117 in the area of interest. The array of locations 117 is represented in FIG. 2 by "spots" 138 of component light beams 130 on the area of interest 113, the spots 138 being distributed in Nx rows and Mx columns, where 'x' is an integer designating the row or column number. It will be appreciated that although FIG. 2 shows a 30×30 array of spots 138, and FIG. 1 shows 20 light component beams in the row R1, each component light beam 130 corresponds to a spot 138 in the row Nx.

In particular, the light sources 110a, 110b will first emit the row R1 of component light beams 130 corresponding to a first row N1 of spots 138 in the array 117, and the detector 114 detects the intensities of component light beams 130 reflected therefrom. The system 100 then shifts so that the component light beams 130 emit a second row N2 of spots 138 in the array 117, and the detector 114 again detects the intensities of the component light beams 130 reflected therefrom. The system 100 again shifts so that the component light beams 130 emit a third row N3, and continues in sequence for x number of rows. The intensities for each spot 138 in the array 117 is detected by the detector 114, which produces a corresponding output signal.

A local controller 132 is in communication with the light sources 110*a*, 110*b* and the detector 114 to control and coordinate various functions of the system 100. For instance, the local controller 132 controls simultaneous operation of the light sources 110*a*, 110*b* together with operation of the imaging detector 114. The local controller 132 may for example be a programmable microcontroller specifically programmed to carry out functions of particular functions of system 100.

As light is emitted by the light sources 110*a*, 110*b*, a portion of the component light beams 130 is reflected by the plant matter 115 and detected by the detector 114. The detector 114 comprises an imaging photodiode array, an objective lens and a filter 132. As mentioned above, the output signal generated by the detector 114 is representative of the intensities of the component light beams 130 reflected from the array of locations 117. The detector 114 communicates the output signal to the local controller 132, which then communicates information regarding the signal to the outcome determination system 116 for processing.

As described above, the pairs of corresponding lasers 120*a/b*, 122*a/b*, 124*a/b* are operated in sequence with other pairs of corresponding lasers at a predetermined operation period, such as 200 microseconds. Therefore, it is possible for the system 100 to correlate a detected intensity with a respective wavelength so that wavelength specific intensity information is obtained by the detector 114 and communicated to the controller 132.

In particular, an objective lens of the detector 114 is arranged to image the spots 138 at which the component beams 130 are reflected by the plant matter 115 onto the photodiode array. In this example, the objective lens is arranged so that each component light beam 130 is reflected at a position approximately 60 cm (±20 cm) below the device 100 are imaged onto respective cells of the photodiode array. Consequently, it is possible to detect intensities arising from respective reflections on the plant matter 115. Moreover, due to the known geometry of the system 100, and the parallel nature of the component light beams 130, and the sequential scanning of the area of interest 113 by the row R1 of component light beams 130, it is also possible for the system 100 to determine locations of plant matter 115, including any specific plant matter, at which the light was reflected. More specifically, through imaging the spots 138, the detector 114 can also communicate information regarding the locations of the spots 138 to the outcome determination system 116 via the local controller 132. The system 116 is then capable of correlating the intensity information with the relevant location information.

Additionally, through scanning the area of interest 113 with the row R1 of component light beams, a 2-dimensional array 117 of spots 138 will ultimately be directed onto the plant matter 115 by the end of the process, as illustrated in FIG. 2. It is therefore also possible to detect the shape of individual plants within the plant matter. For illustrative purposes, FIG. 2 shows a representation of an individual crop plant 134 and an individual weed 136 onto which the array 117 of component light beams 130 is directed. A group of spots 138 including spots from multiple rows N1, N2, N3 etc., and columns M1, M2, M3 etc., falls onto the crop plant 134 and weed 136. The spots 138 that fall onto the weed 136 may have a different intensity distribution to the spots 138 that fall outside the weed 136. Furthermore, the ratio of intensities across the three wavelengths of light beams may be different for weed 136 than from crop plants 134. Consequently, the spots 138 falling on the weed 136, and the positions of those spots 138, can provide information regarding a shape of the weed 136.

Since information concerning the shape of the weed 136 is also based on the intensities of the spots 138, the output signal of the detector 114 also contains information regarding the shape of the weed 136. In other words, the intensity information and position of the spots can provide information concerning the shape of the weed 136. This information is communicated by the detector 114 to the outcome determination system 132, via the local controller 132, for subsequent processing.

The system 100 now has two types of information for identifying a weed among other plant matter: (1) intensity information; and (2) information regarding a shape of the plant matter 115. The two types of information are captured in the output signal from the detector 114, which is sent via the local controller 12 to the outcome determination system 116, and then processed by the outcome determination system 116. Furthermore, as mentioned above the outcome determination system 116 also receives information concerning the location of each spot 138, and correlates this information with respective intensity information.

It is believed that by combining these two types of information, rather than relying on only one type of information, specific plant can be more accurately identified. Advantageously, if one type of information does not adequately distinguish between the specific matter and other matter, the other type of information may still make the distinction. For example, if particular types of weed and crop have similar shapes, the system 100 may still distinguish between the weed and crop on the basis of intensities.

Figure 3:
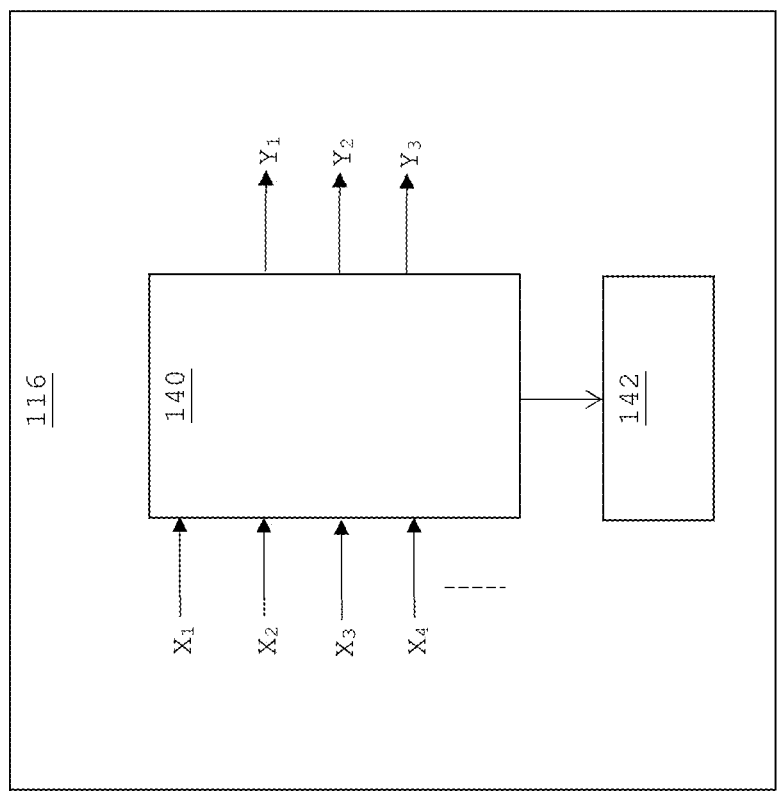
FIG. 3 is a block diagram of an outcome determination system in accordance with an embodiment of the present invention.

With reference to FIG. 3, in this example the outcome determination system 116 may be in the form of a computing device comprising a processor 140 arranged to analyse the information provided by the detector 114. The system 116 also comprises data storage 142 accessible by the processor 140, the data storage 142 containing software program instructions executable by the processor 140. The processor 140 is configured to receive a plurality of inputs '$X_i$', where 'i' is an integer from 1→U, and U represents the total number of inputs. In one example, the total number of inputs T is 30×30×3=2,700, corresponding to the number of spots 138 projected onto the area of interest 113 (e.g. 30×30 spots), and the three different wavelengths of light emitted for each spot 138, detected by the detector 114. The processor 140 then processes the inputs $X_i$ and produces at least one output '$Y_j$', where 'j' is an integer from 1→V, and V represents the total number of outputs. In this example, preferably, each output $Y_j$ provides information indicative of the locations of each spot 138 in a collection of spots 138, which satisfies the following conditions:

(a) the collection of spots 138 maps out a shape of a weed; and (b) a majority of spots in the collection of spots 138 have ratios of detected intensities at the three wavelengths substantially corresponding to known intensities ratios for weed 136.

In this example, to produce the outputs $Y_j$, the processor 140 is configured to execute program instructions based on artificial intelligence techniques, such as but not limited to artificial neural network techniques.

Figure 4:
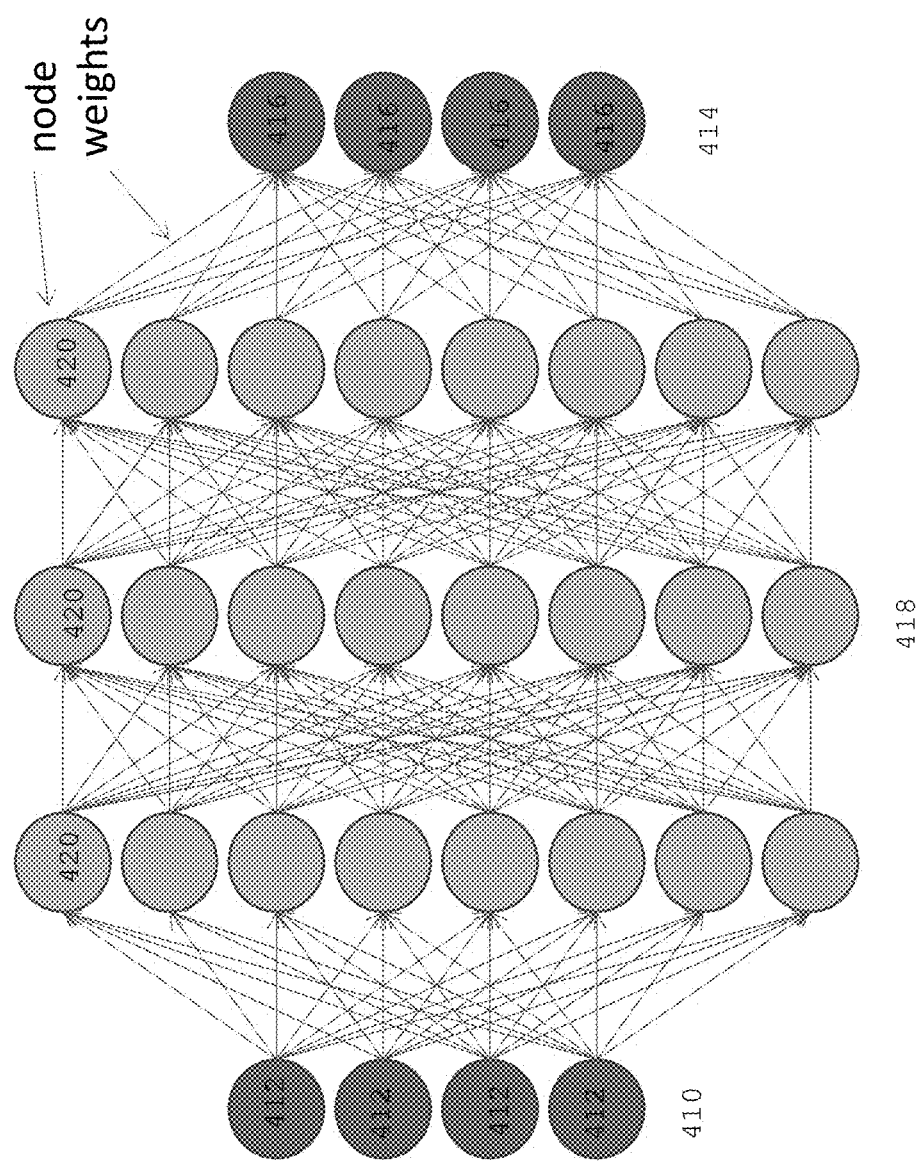
FIG. 4 is a schematic illustration of a neural network, which may be used in an embodiment of the detection system.

As will be familiar to a person skilled in the art, in an artificial neural network 400, there is typically an input layer 410 with multiple input nodes 412, an output layer 414 with multiple output nodes 416, and a hidden layer 418 of weighted nodes 420 providing a network of nodes interconnecting the input layer 410 and output layer 414, as shown in FIG. 4.

To produce meaningful outcomes, the neural network 400 is first trained using training data. This involves feeding each input node 412 with an input value, which (in reality) corresponds to a known set of desired outputs values. The neural network 400 assigns random weights to the weighted nodes 420. The neural network 400 will then calculate a set of output values for the output nodes 416 based on the inputs and random weights. These calculated output values will then be compared to the known set of desired outputs values, and the neural network 400 will systematically adjust the weights of the nodes 420 with a view to causing the next set of calculated output values to be closer to the desired output values.

To train the system 116, a large set of training data is obtained by applying the detection system 100 to test case scenarios. This involves setting up an area of interest having plant matter 115 including multiple crop plants 134 and weeds 136, emitting the array of N (rows)×M (columns) light beams towards the area of interest, and detecting the reflection of component light beams 130 using the detector 114. The output signal from the detector 114 comprises information that can be used as the input values $X_i$ of the system 116 (i.e. input nodes 412 of the neural network 400). Random weights will be assigned to weighted nodes 420 by the processor 140, and output values $Y_j$ (i.e. the output nodes 416) are calculated. Since it is known in the setup which plant matter corresponds to crop 134 and which correspond to weed 136, it is also known which spots 138 of light beams in the array correspond to weed 136. This information represents the desired output of the training data, which is compared to the calculated output values. The neural network 400 adjusts the values of the weighted nodes 420 and repeats the process to converge the calculated output to the desired output.

The system 116 can be trained further by rearranging the test setup and re-running with additional test data. Once the system 116 is trained, it can be applied to real-world scenarios.

Additionally, the detection system 100 may further comprise a plurality of chemical dispensers, such as but not limited to nozzles. The dispensers may be arranged to dispense a chemical substance, such as weed killer, towards a particular location corresponding to one or more spots 138 detected as falling onto plant matter 115 identified as weed 136.

It will be understood to persons skilled in the art of the invention that many modifications may be made without departing from the spirit and scope of the invention.

Figure 5:
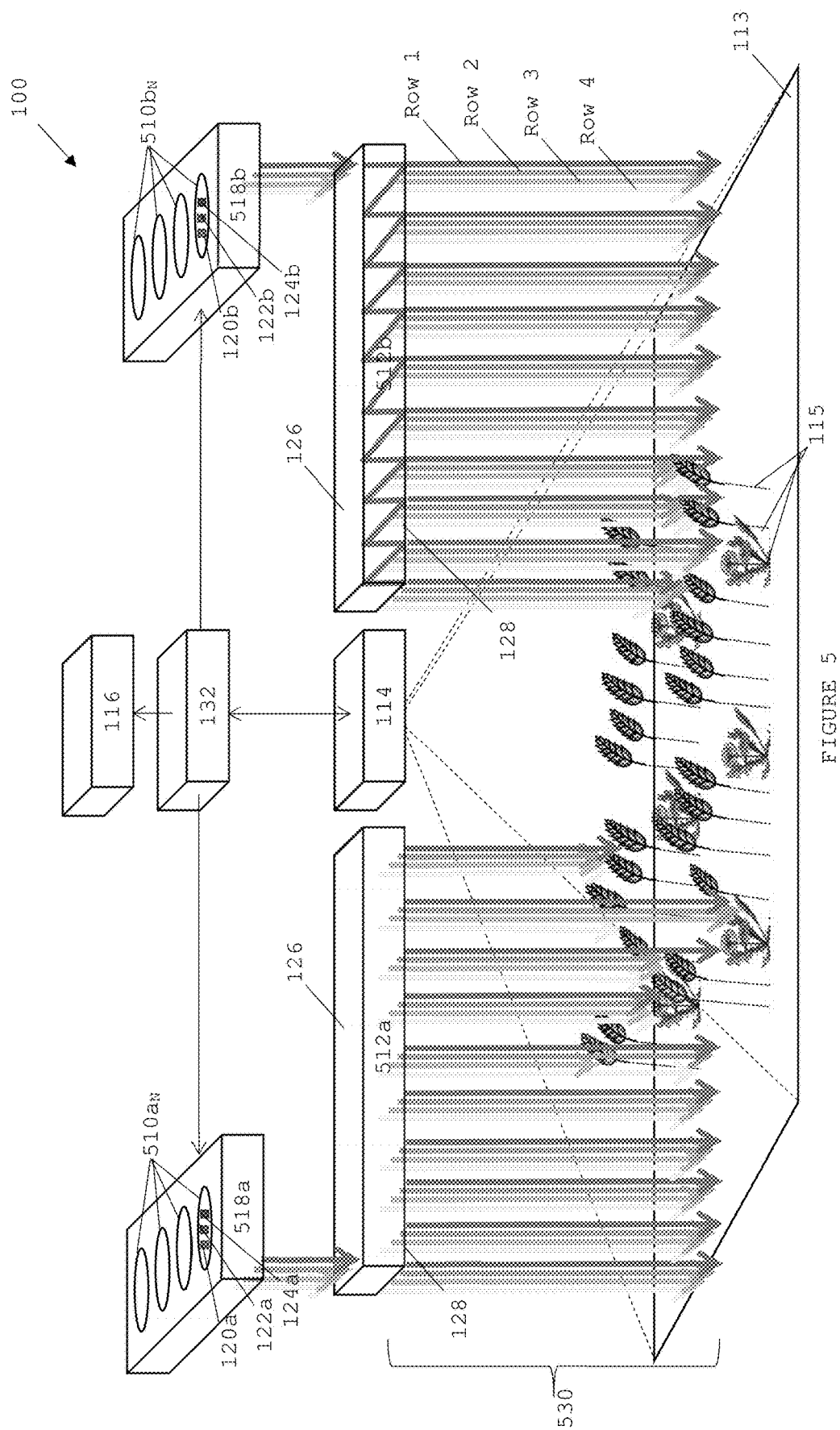
FIG. 5 is a schematic diagram of an embodiment of another detection system in accordance with an embodiment of the present invention.

For example, FIG. 5 shows a system 500, which is similar to the system 100, except that the system 500 is arranged to emit a plurality of light beams distributed in a 2-dimensional manner, instead of the system 100 scanning or traversing the area of interest 113. The same reference numerals will be used for common components.

In particular, in the system 500, the plurality of light beams is distributed in an array of N×M light beams, for example, 30×30 light beams. To distribute the array of light beams, the system 500 comprises a first light emitting module 518a and a second light emitting module 518b. The first module 518a comprises a plurality of the light sources $510a_1, 510a_2, \ldots, 510a_N$, aligned with one another such that N represents the number of rows in the array of light beams. Likewise, the second module 510b also comprises a plurality of the light sources $512b_1, 512b_2, \ldots, 512b_N$.

To distribute the light beams into M columns and project the light beams onto the plant matter 115, the system 100 further comprises two optical elements: a first optical element 512a and a second optical element 512b. In this example, each optical element 512a, 512b is implemented as an optical cavity. The first optical element 112a is arranged to receive light beams from the light sources $510a_N$. The second optical element 112b is arranged to receive light beams from the light sources $510b_N$.

Like the system 100, the optical elements 518a, 518b of the system 500 distribute light beams from each light source in a zigzag manner. However, because there are now multiple light sources $510a_N$, $510b_N$ associated with each light emitting module 118a, 118b, the optical elements 512a, 512b distribute an array of light beams.

Due to the plurality of light sources 110a, 110b of each light emitting module 518a, 518b, and the plurality of beams distributed in a zigzag manner by each light source and respective optical element 512a, 512b, an array of N×M light beams is thus directed to the area of interest 113. An array of spots similar to the array 117 of spots 138 shown in FIG. 2 can thus be imaged by the detector 114. Consequently, information regarding a shape of the matter can also be obtained.

As another example, instead of an array of 30×30 light beams, each light source may only emit one light beam, which scans the area of interest. For example, the specific plant matter to be identified may be crop plants instead of weed.

Also, in other embodiments, the inputs $X_i$ of the processor 140 may be different. For example, instead of N×M×3 inputs, the outcome determination system 116 may further comprise an intensity ratio determiner. The ratio determiner may be configured to determine the intensity ratios corresponding to each spot 138 prior to the inputs being fed into the processor 140. The processor 140 may then receive N×M number of inputs corresponding to the intensity ratios of each spot 138.

In yet another example, other artificial intelligence techniques can be utilised instead of or in addition to neural network techniques, such as but not limited to Support Vector Machine (SVM) algorithms, and Normalised Difference Vegetation Indices (NDVIs).

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

What is claimed is:

1. A detection system for detecting matter and distinguishing specific matter from other matter, the detection system comprising:
   at least one light source arranged to emit one or more light beams having a known wavelength or wavelength range;
   at least one reflector comprising a cavity with reflective coatings for reflection of light from the at least one light source and configured to receive the one or more light beams and direct a plurality of light beams onto a plurality of locations within an area of interest including the matter, the at least one reflector being configured to arrange the plurality of light beams in a row;

a detector for detecting intensities of the one or more light beams reflected at the plurality of locations within the area of interest including the matter; and an electronic circuitry comprising a processor and a data storage containing software program instructions for execution by the processor, wherein the processor is arranged to analyse information provided by the detector, the electronic circuitry being configured to determine whether the matter is specific matter using an artificial neural network;

wherein the system is arranged to obtain information indicative of at least a portion of a shape of at least some of the matter based on detected light intensities of the one or more light beams reflected at the plurality of locations;

wherein the system is arranged to obtain information indicative of a spectral intensity distribution based on detected light intensities of the one or more light beams reflected at the plurality of locations;

wherein the electronic circuitry is arranged to determine whether the matter is specific matter based on the information indicative of at least a portion of a shape of at least some of the matter and based on the information indicative of a spectral intensity distribution;

wherein the system is configured to scan the area of interest with the row of light beams in a direction substantially perpendicular to the row; and wherein the light source is capable of emitting light having at least 3 wavelengths and the electronic circuitry is arranged to determine ratios of detected intensities at the three wavelengths.

2. The detection system of claim 1, wherein the matter is plant matter.

3. The detection system of claim 1, wherein the specific matter is or includes a weed.

4. The detection system of claim 1, wherein the light beams of the plurality of light beams are distributed in a 2-dimensional manner.

5. The detection system of claim 4, wherein the 2-dimensional manner is an array.

6. The detection system of claim 5 wherein the array is an array of N×M light beams, where A is an integer between 1 and 50, and B is an integer between 1 and 50.

7. The detection system of claim 1, wherein the electronic circuitry is configured to receive a plurality of inputs, wherein each input comprises information indicative of an intensity detected at one of the plurality of locations.

8. The detection system of claim 1, wherein the electronic circuitry is arranged to determine whether the matter is specific matter by receiving a plurality of inputs, each input corresponding to one of the one or more light beams reflected at the plurality of locations, wherein each input comprises:

information indicative of an intensity, or a ratio of intensities, of the respective light beam; and information indicative of a location at which the one light beam is reflected.

* * * * *